United States Patent [19]

Shiraishi et al.

[11] 4,092,354

[45] May 30, 1978

[54] PROCESS FOR PRODUCTION OF ACRYLIC ACID

[75] Inventors: Tatsuo Shiraishi; Susumu Kishiwada; Yoshihiko Nagaoka, all of Niihama, Japan

[73] Assignee: Sumitomo Chemical Company, Limited, Japan

[21] Appl. No.: 456,270

[22] Filed: Mar. 29, 1974

[30] Foreign Application Priority Data

Mar. 30, 1973 Japan .................................. 48-36925

[51] Int. Cl.$^2$ ............................................. C07C 51/32
[52] U.S. Cl. ............................... 260/530 N; 252/443; 252/456; 252/468; 252/470; 260/533 N
[58] Field of Search ....................... 260/530 N, 533 N; 252/468, 470

[56] References Cited

U.S. PATENT DOCUMENTS

| 3,087,964 | 4/1963 | Koch et al. | 260/530 N |
| 3,833,649 | 9/1974 | Wada | 260/530 N |
| 3,875,220 | 4/1975 | White | 260/530 N |
| 3,954,855 | 5/1976 | Wada et al. | 260/530 N |

FOREIGN PATENT DOCUMENTS 1,366,301  6/1964  France ............................ 260/533 N Primary Examiner—Vivian Garner
Attorney, Agent, or Firm—Birch, Stewart, Kolasch and Birch

[57] ABSTRACT

A process for production of acrylic acid by the gas phase catalytic oxidation of acrolein with molecular oxygen in the presence of a catalyst, characterized in that the catalyst is a metal oxide catalyst containing as the metal elements Mo, V, Cu and X in a ratio of 12 : 0.1–16 : 0.1–8 : 0.01–12 as the number of atoms (wherein X represents at least one element selected from the group consisting of Fe, Co, Ni and Mg), whereby acrylic acid can be produced at a greatly lowered reaction temperature in a markedly increased yield with an improved perpass yield.

10 Claims, 1 Drawing Figure

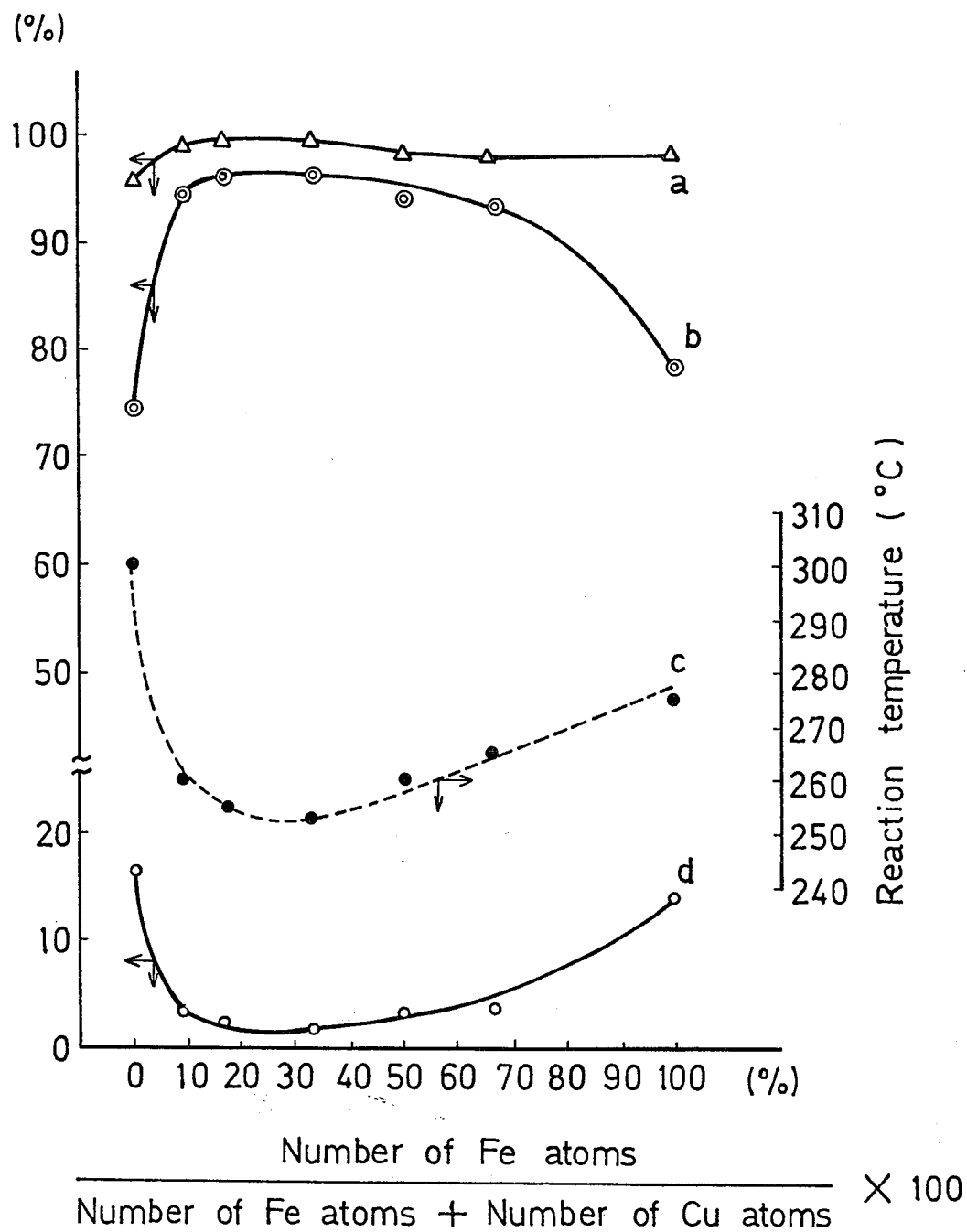

PROCESS FOR PRODUCTION OF ACRYLIC ACID

The present invention relates to a process for production of acrylic acid by the gas phase catalytic oxidation of acrolein at an elevated temperature by the use of a novel catalyst.

Hitherto, a variety of methods have been proposed for production of acrylic acid by the gas phase catalytic oxidation of acrolein at a high temperature. For example, in British Pat. No. 903,034, there is disclosed a method in which a composition comprising molybdenum and one or more multivalent metals selected from the group consisting of vanadium, iron, cerium, tungsten, bismuth, tin and antimony and oxygen is employed as the catalyst. According to this method, however, the use of a molybdenum-vanadium oxide catalyst can afford acrylic acid in a yield of only 28.5%, the conversion of acrolein and the selectivity to acrylic acid being 59.6% and 47.8%, respectively. Further, by the use of a molybdenum-iron oxide catalyst, the yield of acrylic acid is only 8.7%, the conversion of acrolein and the selectivity to acrylic acid being 61.1% and 14.2%, respectively. In addition, all of the working examples in this patent deal with catalysts containing only one multivalent metal and not with catalysts containing two or more multivalent metals at the same time. On the other hand, in Japanese patent No. 1775/1966, there is reported the production of acrylic acid in a perpass yield of 76.4% by the use of a molybdenum-vanadium oxide catalyst. Further, in Japanese patent No. 16604/1967, it is shown (in the reference example) that a molybdenum-vanadium oxide catalyst reveals, when used together with a silica carrier, an initial catalytic activity of 77.2% in yield of acrylic acid but loses the activity with the lapse of time to reduce the yield to 18.5% after 136 hours.

For improving these drawbacks of such molybdenum-vanadium oxide catalysts, there have been made various proposals, several examples of which are as follows: using the catalyst together with a specific aluminum sponge carrier; contacting a mixture of gaseous starting materials with the catalyst at a high temperature; executing the preparation of the catalyst in the presence of a nitrogen-containing base and treating the catalyst in an atmosphere of hydrogen or a lower hydrocarbon, etc. (cf. British patent No. 1,084,143, Japanese patent Nos. 11647/1969, 16096/1970, 30698/1970 and 41299/1970). However, these procedures require complicated operations, and besides, the catalyst exhibits a largely varied catalytic activity depending on the situation, which reveals the difficulty in obtaining a desired catalytic activity constantly.

In order to overcome these disadvantages, there has been proposed the incorporation of various elements as the third and fourth components into the molybdenum-vanadium oxide catalyst. For example, iron, nickel or copper is employed as the third component to be incorporated into the catalyst (cf. Japanese patent Nos. 22457/1971, 18721/1972, 30515/1972 and 48371/1972). However, the preparation of such a catalyst requires the use of a specific heteropolyacid salt as the starting material or the treatment with a gaseous mixture of oxygen and a lower hydrocarbon, and the obtained catalyst is insufficient in the catalytic activity and the selectivity and is not suitable for industrial use. For instance, the catalyst comprising molybdenum, vanadium, iron and oxygen described in Japanese patent No. 30515/1972 affords the conversion of acrolein and the yield of acrylic acid in the amount of 89.3% and 78.0%, respectively. In case of the catalyst comprising molybdenum, vanadium, copper and oxygen as disclosed in Japanese patent No. 48371/1972, the conversion of acrolein is 97.2%, but the yield of acrylic acid is 84.3%. By the catalyst comprising molybdenum, vanadium, copper and oxygen described in Japanese patent No. 18721/1972, the conversion of acrolein and the yield of acrylic acid are 83.0% and 74.7%, respectively, and the reproducibility of the catalytic activity is insufficient.

As the result of studies seeking a catalyst for production of acrylic acid of this type, which is industrially utilizable, it has now been found that, by employing a metal oxide catalyst containing as the metal elements molybdenum, vanadium, copper and at least one member selected from the group consisting of iron, cobalt, nickel and magnesium, acrylic acid can be produced at a greatly lowered reaction temperature in a markedly increased yield with an improved perpass yield. It has also been found that the catalyst has a prolonged catalytic life, and the reproducibility of the catalytic activity is satisfactory.

For instance, a metal oxide catalyst in tablet form (5 mm$\phi$ × 5 mmh) having a composition for the metal elements corresponding to the formula: $Mo_{12}V_4Cu_2Fe_1$ in the ratio of the numbers of atoms can afford a conversion of acrolein of 99.8%, a selectivity to acrylic acid of 97.2% and a yield of acrylic acid of 97.0% at a temperature of 250° C under a space velocity of 1000 hr$^{-1}$ with very little formation of by-products such as acetic acid, carbon monoxide and carbon dioxide.

The mechanism of the action of the catalyst of the invention is still uncertain. Supposedly, copper and the component X (i.e. at least one of iron, cobalt, nickel and magnesium) produce such an excellent synergistic effect in the presence of oxides of molybdenum and vanadium that the reaction can proceed at a markedly lowered temperature with an increased conversion of acrolein and an excellent selectivity to acrylic acid. This is explained further in detail by way of the figure in the accompanying drawing.

In FIG. 1, the axis of the abscissa indicates the value calculated according to the following equation:

$$\frac{\text{(Number of iron atoms)}}{\text{(Number of iron atoms)} + \text{(Number of copper atoms)}} \times 100 \, (\%)$$

wherein the number of iron atoms and the number of copper atoms are those when the number of molybdenum atoms is taken as 12. The ordinate at the left hand side indicates the percent (%) and that at the right hand side the reaction temperature. The curved lines a, b, c and d represent the conversion of acrolein, the yield of acrylic acid, the reaction temperature and the total selectivity to carbon monoxide and carbon dioxide, respectively. The catalysts tested have the compositions for the metal elements corresponding to the following formulae: $Mo_{12}V_4Cu_2$, $Mo_{12}V_4Cu_2Fe_{0.2}$, $Mo_{12}V_4Cu_2Fe_{0.4}$, $Mo_{12}V_4Cu_2Fe_1$, $Mo_{12}V_4Cu_2Fe_2$, $Mo_{12}V_4Cu_2Fe_4$ and $Mo_{12}V_4Fe_1$. With each of these catalysts, the conversion of acrolein, the yield of acrylic acid and the total selectivity to carbon monoxide and carbon dioxide are determined and shown in FIG. 1 together with the reaction temperature.

As obviously seen in FIG. 1, in case of the catalyst comprising only molybdenum, vanadium and copper or iron, the conversion of acrolein is small and the yield of acrylic acid is extremely low in spite of the high reaction temperature, while the amount of the by-products such as carbon monoxide and carbon dioxide is large. On the contrary, when both copper and iron are incorporated into oxides of molybdenum and vanadium, the conversion of acrolein becomes large and the yield of acrylic acid is greatly increased in spite of the extremely low reaction temperature, while the by-production of carbon monoxide and carbon dioxide is remarkably inhibited, which reveals an excellent synergistic effect between copper and iron. Such an effect can be also obtained between copper and a component X other than iron.

Although the molybdenum-vanadium oxide catalyst is known to have a short catalytic life, as shown in Japanese patent No. 16604/1967, the catalyst of the invention can afford a conversion of acrolein of 98.5% and a yield of acrylic acid of 94.8% even after being continuously used at a temperature of 255° C under a space velocity of 1000 hr$^{-1}$ for about 1000 hours and is satisfactorily utilizable for industrial purposes.

As understood from the above, it is a great advantage of the catalyst of the invention that it has a sufficient catalytic life and can afford acrylic acid of high purity in a high yield at an extremely low reaction temperature. In addition, the preparation of the catalyst of the invention can be accomplished by a quite simple procedure. Thus, the present invention provides an industrially advantageous process for the production of acrylic acid from acrolein.

According to the present invention, there is provided a process for production of acrylic acid by the gas phase catalytic oxidation of acrolein with molecular oxygen which comprises contacting a gaseous mixture of acrolein and molecular oxygen with a metal oxide catalyst containing as the metal elements Mo, V, Cu and X in a ratio of 12 : 0.1-16 (preferably 0.5-12) : 0.1-8 (preferably 0.2-6) : 0.01-12 (preferably 0.05-8) as the number of atoms (wherein X represents at least one element selected from the group consisting of Fe, Co, Ni and Mg) and the number of oxygen atoms is determined in dependence upon the number of the other metallic elements, i.e., by the valence requirements thereof.

For the preparation of the catalyst to be used in this invention, there are employed a molybdenum source (e.g. ammonium molybdate, molybdenum oxide, molybdic acid), a vanadium source (e.g. ammonium metavanadate, vanadium pentoxide), a copper source (e.g. copper chloride, copper oxide, copper nitrate, copper carbonate, copper acetate) and one or more sources for the metal elements X such as nitrates, carbonates, chlorides, oxides and organic acid salts of iron, cobalt, nickel and magnesium.

The caytalyst may be composed of the said essential sources only but favorably further with a suitable carrier (e.g. silica sol, silica gel, alumina, alumina siicate, silicon carbide, diatomaceous earth, or titanium oxide). Silica sol is a particularly preferred carrier. The amount of the carrier is varied with its kind and may be usually less than 90% by weight, preferably from 5 to 90% by weight, of the catalyst.

The preparation of the catalyst may be effected by a per se conventional procedure, of which a typical example is as follows: dissolving suitable amounts of ammonium molybdate and ammonium metavanadate in water under heating, adding thereto an aqueous solution of cupric nitrate and ferric nitrate, adding thereto silica sol as the carrier, evaporating the resultant mixture on a sand bath at 100° to 150° C, calcining the obtained cake at 250° C for 3 hours, crushing the product, admixing the crushed product with graphite in an amount of about 2% by weight with respect to the amount of the catalyst, molding the mixture into tablets of 5 mm in diameter and 5 mm in height and calcining the tablets at 400° C for 6 hours in air.

The production of acrylic acid using the catalyst of the invention may be carried out by a fluidized bed process or a fixed bed process. The particle size of the catalyst is not particularly limited and may be optionally varied with the type of its use.

The acrolein used as the starting material in the process of the invention does not necessarily have to be pure, and there may be employed a gaseous mixture which is obtained by catalytic oxidation of propylene with air and which contains acrolein, unreacted propylene, carbon monoxide, carbon dioxide, nitrogen and steam.

As the oxygen source, the use of air is usual, but pure oxygen diluted or not with an inert gas such as carbon dioxide or nitrogen may be also employed.

The gaseous mixture to be contacted with the catalyst may comprise 0.5 to 10 mol % of acrolein, 0.5 to 20 mol % of oxygen and 0 to 90 mol % (preferably 20 to 70 mol %) of steam.

The reaction temperature for the catalytic oxidation is varied depending on the compositions of the catalyst and the gaseous starting materials, the space velocity and the like and may be usually 200° to 400° C, preferably 220° to 350° C. The space velocity may be 300 to 12,000 hr$^{-1}$, preferably 500 to 6,000 hr$^{-1}$.

In this specification, the conversion of acrolein, the selectivity to acrylic acid and the yield of acrylic acid are calculated by the following equations, respectively:

$$\text{Conversion of acrolein} = \frac{\text{Reacted acrolein (mol)}}{\text{Feed acrolein (mol)}} \times 100 \, (\%)$$

$$\text{Selectivity to acrylic acid} = \frac{\text{Produced acrylic acid (mol)}}{\text{Reacted acrolein (mol)}} \times 100 \, (\%)$$

$$\text{Yield of acrylic acid} = \frac{\text{Produced acrylic acid (mol)}}{\text{Feed acrolein (mol)}} \times 100 \, (\%)$$

The analysis of the product is effected by gas chromatography, and for acid determination, the alkali titration method is adopted.

Practical and presently preferred embodiments of the invention are illustratively shown in the following Examples.

EXAMPLE 1

Ammonium metavanadate (11.70 g) and ammonium molybdate (52.97 g) are dissolved in hot water (300 ml), and a solution of cupric nitrate (12.08 g) and ferric nitrate (2.02 g) in water (50 ml) is added thereto. To the resultant dispersion, silica sol (6.7 ml) containing 20% by weight of SiO$_2$ is added, and the mixture is evaporated on a sand bath at 100° to 150° C. The residue is calcined at 250° C for 3 hours, crushed into powders, admixed with about 2% by weight of graphite and molded into tablets of 5 mm in diameter and 5 mm in height, which are calcined at 400° C for 6 hours in air to give a catalyst having a composition of the metal elements corresponding to the formula: $Mo_{12}V_4Cu_2Fe_{0.2}$, the ratio of silica as the carrier to molybdenum being 1 : 12 ($Si_1 : Mo_{12}$).

In a glass made reaction tube of 19 mm in inner diameter, the above obtained catalyst (15 ml) is charged, and a gaseous mixture comprising 5 mol % of acrolein, 40 mol % of air and 55 mol % of steam is introduced therein at 260° C under a space velocity of 1000 $hr^{-1}$ to effect the oxidation whereby the following results are obtained: conversion of acrolein, 99.1%; yield of acrylic acid, 94.4%; selectivity to acrylic acid, 95.3%; total selectivity to carbon monoxide and carbon dioxide, 3.2%.

EXAMPLES 2 to 5

As in Example 1, the preparation of a catalyst is carried out with a varied amount of ferric nitrate to obtain a catalyst having a composition for the metal elements corresponding to the formula: $Mo_{12}V_4Cu_2Fe_{0.4}$, $Mo_{12}V_4Cu_2Fe_1$, $Mo_{12}V_4Cu_2Fe_2$ or $Mo_{12}V_4Cu_2Fe_4$.

Using the thus obtained catalyst, the oxidation reaction is effected as in Example 1. The results are shown in Table 1.

Table 1

| No. | Composition of catalyst (for metal elements) | Reaction temp. (° C) | Conversion of acrolein (%) | Yield of acrylic acid (%) | Selectivity to acrylic acid (%) | Selectivity to CO + $CO_2$ (%) |
|---|---|---|---|---|---|---|
| 2 | $Mo_{12}V_4Cu_2Fe_{0.4}$ | 255 | 99.5 | 95.9 | 96.4 | 2.4 |
| 3 | $Mo_{12}V_4Cu_2Fe_1$ | 250 | 99.8 | 97.0 | 97.2 | 1.7 |
| 4 | $Mo_{12}V_4Cu_2Fe_2$ | 260 | 98.5 | 94.0 | 95.4 | 3.3 |
| 5 | $Mo_{12}V_4Cu_2Fe_4$ | 265 | 98.4 | 93.5 | 95.0 | 3.6 |

REFERENCE EXAMPLE 1

The preparation of a catalyst is effected three times as in Example 1 but not using ferric nitrate to obtain a catalyst having a composition for the metal elements corresponding to the formula: $Mo_{12}V_4Cu_2$.

Using each of the thus obtained three catalysts, the oxidation reaction is carried out as in Example 1. The results are as follows (wherein the figures indicate the average values with standard deviation on the three catalysts): reaction temperature affording the highest yield of acrylic acid, 300 ± 19° C; conversion of acrolein, 95.8 ± 1.4%; selectivity to acrylic acid, 77.7 ± 11.0%; yield of acrylic acid, 74.5 ± 11.4%; total selectivity to carbon monoxide and carbon dioxide, 16.2 ± 8.7%.

These results apparently show that the catalyst comprising only molybdenum, vanadium and copper is inferior in catalytic activity and selectivity to the objective compound, and the reproducibility of the catalytic activity is extremely bad.

REFERENCE EXAMPLE 2

The preparation of a catalyst is effected as in Example 1 except that cupric nitrate is not employed and the amount of ferric nitrate is changed from 2.02 g to 10.11 g to obtain a catalyst having a composition for the metal elements corresponding to the formula: $Mo_{12}V_4Fe_1$.

Using this catalyst, the oxidation reaction is carried out at a temperature of 275° C whereby the following results are obtained: conversion of acrolein, 98.0%; yield of acrylic acid, 78.5%; total selectivity to carbon monoxide and carbon dioxide, 14.1%.

It is understood from the results that the yield of acrylic acid is low in case of the catalyst comprising only molybdenum, vanadium and iron.

EXAMPLE 6

The catalyst having the same composition for the metal elements as that of the catalyst in Example 3 is prepared five times, and the reproducibility of the catalytic activity is examined whereby the following results are obtained: reaction temperature affording the highest yield of acrylic acid, 256 ± 7° C; conversion of acrolein, 99.4 ± 0.4%; yield of acrylic acid, 96.2 ± 0.8%.

EXAMPLE 7

The preparation of a catalyst is effected as in Example 1 but using cobalt nitrate (2.91 g) in place of ferric nitrate (2.02 g) to obtain a catalyst having a composition for the metal elements corresponding to the formula: $Mo_{12}V_4Cu_2Co_{0.4}$.

Using the thus obtained catalyst, the oxidation reaction is carried out at 265° C as in Example 1 whereby the following results are obtained: conversion of acrolein, 98.7%; yield of acrylic acid, 94.1%.

EXAMPLE 8

The preparation of a catalyst is effected as in Example 1 but using nickel nitrate (7.27 g) in place of ferric nitrate (2.02 g) to obtain a catalyst having a composition for the metal elements corresponding to the formula: $Mo_{12}V_4Cu_2Ni_1$.

Using the thus obtained catalyst, the oxidation reaction is carried out at 270° C as in Example 1 whereby the following results are obtained: conversion of acrolein, 98.8%; yield of acrylic acid, 93.8%.

EXAMPLE 9

The preparation of a catalyst is effected as in Example 1 but using ferric nitrate (5.06 g), cobalt nitrate (3.64 g) and nickel nitrate (3.63 g) in place of ferric nitrate (2.02 g) to obtain a catalyst having a composition for the metal elements corresponding to the formula: $Mo_{12}V_4Cu_2Fe_{0.5}Ni_{0.5}Co_{0.5}$.

Using the thus obtained catalyst, the oxidation reaction is carried out at 270° C as in Example 1 whereby the following results are obtained: conversion of acrolein, 99.3%; yield of acrylic acid, 94.5%.

EXAMPLE 10

The preparation of a catalyst is effected as in Example 1 but using magnesium nitrate (6.41 g) in place of ferric nitrate (2.02 g) to obtain a catalyst having a composition for the metal elements corresponding to the formula: $Mo_{12}V_4Cu_2Mg_1$.

Using the thus obtained catalyst, the oxidation reaction is carried out at 265° C as in Example 1 whereby the following results are obtained: conversion of acrolein, 99.5%; yield of acrylic acid, 95.3%.

EXAMPLE 11

The preparation of a catalyst is effected as in Example 3 but not using silica sol as the carrier, and the oxidation reaction is carried out in the presence of the obtained catalyst at 265° C whereby the following results are obtained: conversion of acrolein, 99.2%; yield of 94.7%.

EXAMPLE 12

The preparation of a catalyst is effected as in Example 3 but using 100 ml of silica sol as the carrier to obtain a catalyst having a composition for the metal elements corresponding to the formula: $Mo_{12}V_4Cu_2Fe_1$, the ratio of silica as the carrier to molybdenum being 15 : 12 ($Si_{15} : Mo_{12}$).

Using the thus obtained catalyst, the oxidation reaction is carried out at 270° C as in Example 1 whereby the following results are obtained: conversion of acrolein, 98.9%; yield of acrylic acid, 93.4%.

EXAMPLES 13 to 15

The preparation of a catalyst is effected as in Example 1 but varying the amount of ammonium metavanadate, cupric nitrate or ferric nitrate, and the oxidation reaction is carried out in the presence of the obtained catalyst as in Example 1. The results are shown in Table 2.

Table 2

| No. | Composition of catalyst (for metal elements) | Reaction temp. (° C) | Conversion of acrolein (%) | Yield of acrylic acid (%) | Selectivity to acrylic acid (%) | Selectivity to CO + CO₂ (%) |
|---|---|---|---|---|---|---|
| 13 | $Mo_{12}V_2Cu_{0.5}Fe_1$ | 275 | 98.9 | 93.5 | 94.5 | 3.7 |
| 14 | $Mo_{12}V_6Cu_2Fe_1$ | 265 | 99.1 | 95.3 | 96.2 | 2.5 |
| 15 | $Mo_{12}V_8Cu_4Fe_2$ | 270 | 99.5 | 94.7 | 95.2 | 3.4 |

EXAMPLE 16

Using the catalyst obtained in Example 3, the oxidation reaction is effected at 280° C under a space velocity of 3000 hr⁻¹ whereby the following results are obtained: conversion of acrolein, 97.5%; yield of acrylic acid, 92.3%.

EXAMPLE 17

Using the catalyst obtained in Example 3, the oxidation reaction is continuously effected at 255° C for about 1000 hours whereby the conversion of acrolein and the yield of acrylic acid are 98.5% and 94.8%, respectively.

What is claimed is:

1. A process for the production of acrylic acid by the gas phase catalytic oxidation of acrolein with molecular oxygen which comprises contacting a gaseous mixture comprising acrolein and molecular oxygen with a catalyst consisting essentially of a metal oxide composition having the formula:

$$Mo_{12}V_{0.1-16}Cu_{0.1-8}X_{0.01-12}O_a,$$

wherein X is at least one member selected from the group consisting of Fe, Co and Ni and $a$ is a number determined by the valence requirements of the other atoms.

2. The process according to claim 1, wherein the metal oxide composition has the formula:

$$Mo_{12} V_{0.5-12} Cu_{0.2-6} X_{0.05-8} O_a.$$

3. The process according to claim 1, wherein the gaseous mixture also contains steam.

4. The process according to claim 3, wherein the gaseous mixture contains from 20 to 70 mol % of steam.

5. The process according to claim 1, wherein the contact is effected at a temperature of 200° to 400° C.

6. The process according to claim 1, wherein the contact is effected at a space velocity of 300 to 12,000 hr⁻¹.

7. The process according to claim 1, wherein the metal oxide catalyst is supported on an inert carrier.

8. The process according to claim 7, wherein said carrier is selected from the group consisting of silica sol, silica gel, alumina, alumina silicate, silicon carbide, diatomaceous earth and titanium oxide.

9. The process according to claim 8, wherein the amount of the carrier is from 5 to 90% by weight based on the weight of the catalyst.

10. The process according to claim 1, wherein the gaseous mixture comprises acrolein, molecular oxygen and steam in a proportion of 0.5–10:0.5–20:0–90 by mol %, respectively.

* * * * *